Dec. 4, 1956 G. DE RUITER Plant Pat. 1,533
ROSE PLANT
Filed Dec. 30, 1955
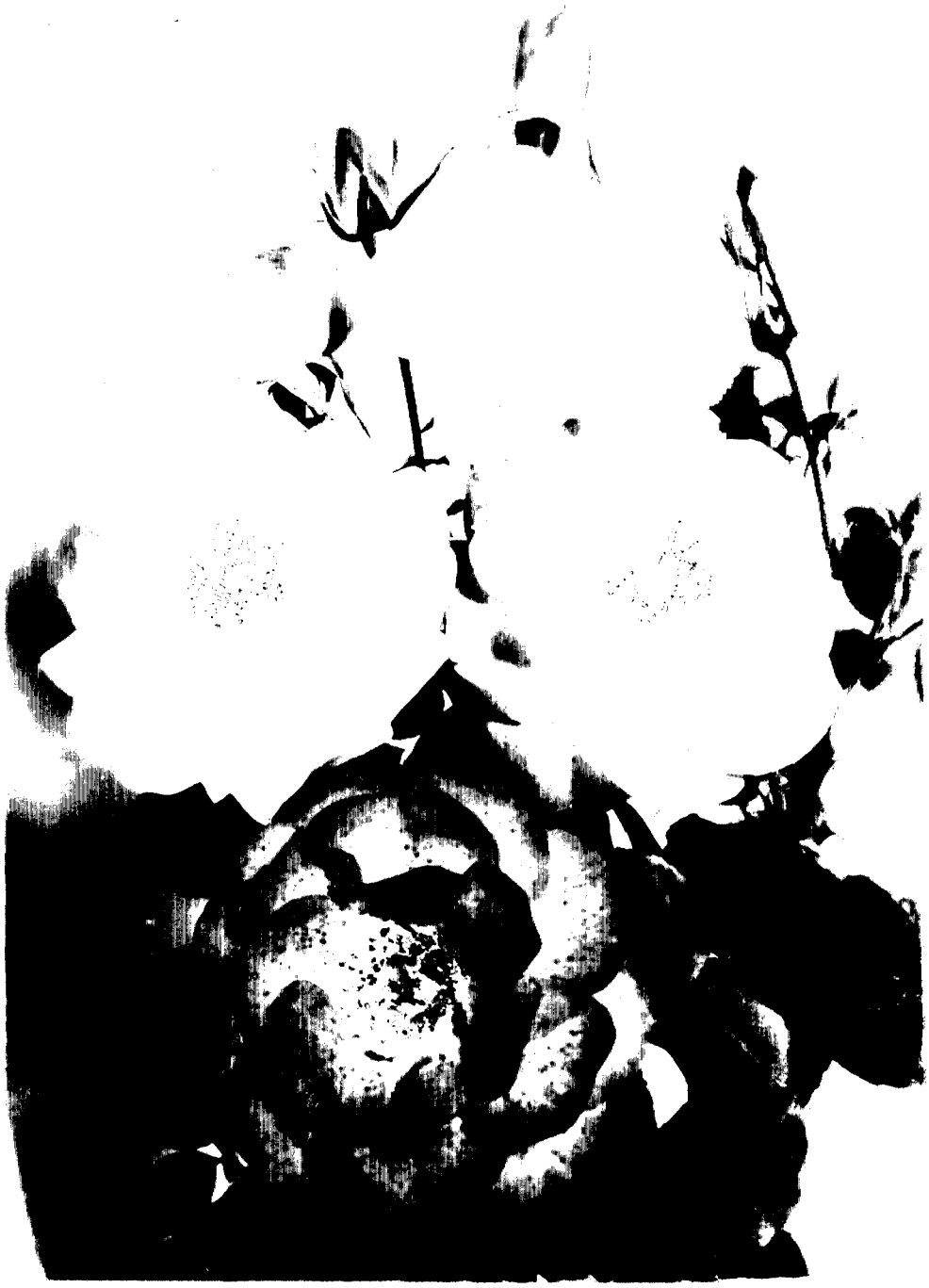
Inventor.
Gerrit de Ruiter
By: Robb & Robb
Attorneys.

United States Patent Office

Plant Pat. 1,533
Patented Dec. 4, 1956

1,533

ROSE PLANT

Gerrit de Ruiter, Hazerswoude, Netherlands, assignor to The Conard-Pyle Company, West Grove, Pa., a corporation of Pennsylvania Application December 30, 1955, Serial No. 556,763

1 Claim. (Cl. 47—61)

The present invention relates to a new and distinct variety of rose plant of the hybrid polyantha class (commonly called floribunda), which was originated by me by crossing the variety "Duisberg" (unpatented) with an unnamed and unpatented polyantha seedling.

As the result of this breeding, I have produced a new rose variety which is particularly characterized as to novelty by a unique and desirable combination of features, the most outstanding of which are as follows:

(1) Its vigorous and good habits of growth;

(2) The abundance, constancy, exceptionally large size and the outstanding sweet fragrance of its flowers which is unusual in a floribunda rose;

(3) The excellent form and unusually heavy substance of the flowers; and (4) The distinctive progressive color change and the complete harmony of the colors at all stages of the flowers as they open and mature, said color change being further characterized by an unusual increase in color intensity instead of the usual fading as the flowers mature.

The foregoing characteristics and distinctions definitely differentiate my new variety from its parents, as well as from all other varieties of its class of which I am aware, and the unique combination of features makes the new variety valuable and desirable for both garden decoration and cut flower use.

Asexual reproduction of the new variety by budding, as performed by me in Holland and as performed on my behalf at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Color Chart of the Royal Horticultural Society:

Type: Hardy; bush; outdoor; seedling; for cut flowers and for garden decoration:
Class: Hybrid polyantha.
Breeding: Seedling.
*Seed parent.*—"Duisberg."
*Pollen parent.*—An unnamed polyantha seedling.
Propagation: Holds its distinguishing characteristics through succeeding propagations by budding.

FLOWER

Locality where grown and observed: West Grove, Pennsylvania, U. S. A.
Flowers borne: Several to stem; in regular clusters; on stems of normal strength and medium length.
Quantity of bloom: Abundant, outdoors.
Continuity: Continuous.
Fragrance: Moderate; Tea type.

Bud:
*Peduncle.*—Medium length; medium caliper; stiff; rough; with numerous hairs of Garnet Brown, Plate 00918/3. Color—Garnet Brown, Plate 00918/3.
*Before calyx breaks.*—Size—medium. Form—medium length; ovoid; with a conspicuous neck; with foliaceous appendages on the surface of the bud; with medium caliper, much-cut, bristle-like foliaceous parts extending beyond the tip of the bud equal to ½ or more of its length.
*As calyx breaks.*—Color—Light Apricot, Plate 609/1 where newly exposed to light, changing to Oxblood Red, Plate 00823.
*As first petal opens.*—Size—medium. Form—medium length; ovoid. Color: Outside—Rose Madder, Plate 23/2, with area of Current Red, Plate 821; inside—Carmine Rose, Plate 621/1 at outer margin, shading into a narrow zone of Rose Pink, Plate 427/3, and thence to Lemon Yellow, Plate 4/2, with base of Lemon Yellow, Plate 4/1.
*Opening.*—Opens up well.
Bloom:
*Size (when fully open).*—Medium; from 2¾ inches to 4 inches.
*Petalage.*—Double; from 23 to 28 petals; arranged regularly.
*Form.*—High-centered at first, but becoming shallow cupped; petals being at first loosely concave, with a more or less angular bend at center, but becoming loosely rolled outward later at maturity.
Petals:
*Texture.*—Thick; with inside satiny and outside velvety.
*Shape.*—Outer petals—obovate; with 1 or 2 notches. Intermediate petals—obovate; with 1 or 2 notches. Inner petals—obovate; irregular; with 1 or 2 notches.

This description of a newly opened flower was made from a rose grown outdoors in the month of August, at West Grove, Pennsylvania, U. S. A.:

*Color.*—Outer petal: Outside surface—Camellia Rose, Plate 622/1, shading to Nasturtium Orange, Plate 610/3 and then to Sulphur Yellow, Plate 1/1 at base; inside surface—Carmine Rose, Plate 621, shading to Camellia Rose, Plate 622/2 and then to Orange Buff, Plate 507/3, with basal area of Canary Yellow, Plate 2/1. Intermediate petal: Outside surface—Maize Yellow, Plate 607/1, more or less touched with Carmine, Plate 21/2 at apex and with basal area of Canary Yellow, Plate 2/1, said Carmine coloring varying between flowers and being progressively less with each row of petals from the outside towards the center of individual blooms, but being constantly in progress of spreading from apex of the petals downward; inside surface—Indian Yellow, Plate 6/2, more or less touched with Carmine, Plate 21/1, and with basal area of Canary Yellow, Plate 2/2, said Carmine coloring constantly and gradually progressing and spreading as in foregoing description of outside surface, but with the amount of Carmine coloring on each petal tending to be less on the inside than on the outside at any one time. Inner petal: Outside surface—Maize Yellow, Plate 607/1, more or less touched with Carmine, Plate 21/1 at outer edge or apex, with basal area of Canary Yellow, Plate 2/1, said Carmine coloring varying between flowers and being progressively less with each row of petals toward the center of the bloom, but being in constant progress of appearing on successive inner petals and of spreading on each petal from apex downward; inside surface—Indian Yellow, Plate 6/3, more or less touched with Azalea Pink, Plate 618/2 at outer edge or apex, with basal area of Canary Yellow, Plate 2/1, and showing the same constant and gradual progression and spread of the Pink coloring as in the foregoing description of the Carmine coloring on the outside surface.

This description was made from a rose that was open for three days outdoors in the month of August, at West Grove, Pennsylvania, U. S. A.:

*Color.*—Outer petal: Outside surface—China Rose, Plate 024/1 at outer margin, shading to Tyrian Rose, Plate 24/3 overlying White, and then to Primrose Yellow, Plate 601/1; inside surface—Carmine, Plate 21/1 on area exposed to sun, with those petals shielded from the sun being White or near White, and with base of petals Canary Yellow, Plate 2/1. Inner petal:—Outside surface—Carmine, Plate 21/2 overlying White and shading more or less to White, with area surrounding base of Primrose Yellow, Plate 601/3; inside surface—Carmine, Plate 21/1 where exposed to light, shading to Carmine, Plate 21/2, but being White or near White where not exposed to sunlight.

*General color effect.*—Newly opened flower—Maize Yellow, Plate 607/2, more or less tinged with Carmine, Plate 21/2, but becoming increasingly tinged with Carmine, Plate 21/2 starting at apex of petals and progressing downwardly thereof, and also progressing from the outer petals toward the center of the flower. 3-days open—Carmine, Plate 21/1, with areas of White or near White where overlapping of petals shade same from light.

*Behavior.*—Drop off cleanly; Red coloring continues to increase and darken until petals fall; in final stages, many blooms show areas that exactly match the very dark coloring of unopened buds, thus completing a full cycle through the series of color changes.

*Flower longevity.*—On bush in garden—4 days in August. Cut roses grown outdoors and kept at living-room temperatures—4 days in August.

REPRODUCTIVE ORGANS

Stamens: Medium number; arranged regularly about pistils.

Filaments: Many; medium length; most with anthers. Color—Lemon Yellow, Plate 4/1.

Anthers: All open at once; medium size. Color—Aureolin, Plate 3/2.

Pollen: Abundant. Color—Indian Yellow, Plate 6.

Pistils: Medium number.

Styles: Uneven; medium length; from thin to medium weight; bunched.

Stigma: Color—Primrose Yellow, Plate 601/3.

Ovaries: All enclosed in calyx.

Hips: Short; globular; with inconspicuous neck; smooth; walls thick and fleshy. Color—Fern Green, Plate 0862/1.

Sepals: Permanent; moderately long; spear-shaped.

Seeds: Few; medium size.

PLANT

Foliage:

*Leaves.*—Generally compound of 5 leaflets; from normal quantity to abundant; medium size; leathery.

*Leaflets.*—Shape—oval, with apex acute. Base—obtuse. Margin—simply serrate.

*Color.*—Mature: Upper surface—Parsley Green, Plate 00962; under surface—Oxblood Red, Plate 00823/1, overlying Willow Green, Plate 000862/1. Young: Upper surface—Spinach Green, Plate 0960, washed with Garnet Brown, Plate 00918; under surface—Oxblood Red, Plate 00827, overlying Scheeles Green, Plate 860/3.

*Rachis (the supporting stem of the compound leaf).*—Medium caliper. Upper side—grooved; hairy. Under side—extremely smooth.

*Stipules.*—Moderately long; narrow; with points of medium length turning out at an angle of 45°.

*Disease resistance.*—Resistant to both mildew and blackspot comparable to average good variety of Foribunda rose, as determined by comparison with other varieties grown under comparable cultural conditions at West Grove, Pennsylvania, U. S. A.

Growth:

*Habit.*—Bushy; upright; much-branched.

*Growth.*—Vigorous.

Canes.—Medium caliper.

*Main Stems.*—Color—Spinach Green, Plate 0960/3. Thorns—Several; medium length; hooked; pointed downward; with oval base of medium length. Prickles—None. Hairs—none.

*Branches.*—Color—Lettuce Green, Plate 861. Thorns—Many; medium length; hooked; pointed downward; with oval base of medium length. Prickles—few. Color—Bronze. Hairs—none.

*New shoots.*—Color—Oxblood Red, Plate 00823/1, overlying Lettuce Green, Plate 861/1. Thorns—several; medium length; hooked; pointed downward; with medium-long oval base. Prickles—none. Hairs—none.

I claim:

A new and distinct variety of rose plant of the hybrid polyantha class, substantially as herein shown and described, characterized particularly as to novelty by the combination of its vigorous and good habits of growth, the abundance, constancy, exceptionally large size and unusually outstanding sweet fragrance of its flowers, the excellent form and unusually heavy substance of its flowers, and the distinctive progressive color change and complete harmony of the colors at all stages of the flowers as they open and mature, with an attendant and unusual increase in color intensity.

No reference cited.